(12) United States Patent
Rasmussen et al.

(10) Patent No.: US 9,161,850 B2
(45) Date of Patent: Oct. 20, 2015

(54) INTRODUCER FOR ENDOVASCULAR IMPLANTS

(75) Inventors: Erik E. Rasmussen, Slagelse (DK); Bent Ohlenschlaeger, Skensved (DK); William K. Dierking, Louisville, KY (US); Blayne A. Roeder, Lafayette, IN (US); David E. Orr, Piedmont, SC (US)

(73) Assignee: Cook Medical Technologies LLC, Bloomington, IN (US)

( * ) Notice: Subject to any disclaimer, the term of this patent is extended or adjusted under 35 U.S.C. 154(b) by 376 days.

(21) Appl. No.: 13/008,366

(22) Filed: Jan. 18, 2011

(65) Prior Publication Data

US 2011/0137403 A1 Jun. 9, 2011

Related U.S. Application Data

(63) Continuation of application No. PCT/US2009/004126, filed on Jul. 16, 2009.

(60) Provisional application No. 61/135,263, filed on Jul. 18, 2008.

(51) Int. Cl.
*A61F 2/06* (2013.01)
*A61F 2/95* (2013.01)
*A61M 25/00* (2006.01)
*A61M 25/01* (2006.01)

(52) U.S. Cl.
CPC .............. *A61F 2/95* (2013.01); *A61M 25/0041* (2013.01); *A61M 25/0138* (2013.01)

(58) Field of Classification Search
CPC ..................... A61M 25/0041; A61M 25/0054; A61M 25/0063; A61M 25/0067; A61M 25/0069; A61M 25/0081; A61M 25/08; A61M 25/0102; A61M 25/0152
USPC .......... 623/1.11; 604/164.01, 164.13, 170.03, 604/510, 523–532; 606/108
See application file for complete search history.

(56) References Cited

U.S. PATENT DOCUMENTS

| 4,033,331 A | * | 7/1977 | Guss et al. ..................... 600/434 |
| 5,040,543 A | | 8/1991 | Badera et al. ................. 600/585 |
| 6,171,329 B1 | | 1/2001 | Shaw et al. .................... 606/213 |

(Continued)

FOREIGN PATENT DOCUMENTS

| AU | 2007/212623 | 8/2007 |
| EP | 0468645 | 1/1992 |

(Continued)

OTHER PUBLICATIONS

International Search Report for PCT/US2009/004126 (PCT WO 2010008571).

*Primary Examiner* — Katherine M Shi
*Assistant Examiner* — Lindsey Bachman
(74) *Attorney, Agent, or Firm* — Brinks Gilson & Lione

(57) ABSTRACT

An introducer assembly for introducing a stent-graft or other device into a vessel of a patient is provided with a dilator tip which is naturally curved, preferably to be substantially a U-shape. The dilator tip is flexible so as to be able to become substantially straight with a guide wire therein and yet to be able to curve back towards its natural curvature during deployment of an implant. The curvature of the dilator tip can ensure that the dilator tip does not cause damage to the vessel wall during deployment of an implant carried thereon, as can occur with straight dilator tips.

14 Claims, 13 Drawing Sheets

(56) References Cited

U.S. PATENT DOCUMENTS

| | | | |
|---|---|---|---|
| 6,458,151 B1 | 10/2002 | Saltiel | 623/1.11 |
| 6,694,983 B2 | 2/2004 | Wolf et al. | 128/898 |
| 7,115,134 B2 * | 10/2006 | Chambers | 606/108 |
| 7,611,529 B2 | 11/2009 | Greenberg et al. | 623/1.11 |
| 2002/0100484 A1 | 8/2002 | Hall et al. | 128/898 |
| 2004/0106974 A1 | 6/2004 | Greenberg et al. | 623/1.11 |
| 2007/0088424 A1 | 4/2007 | Greenberg et al. | 623/1.12 |
| 2007/0198078 A1 | 8/2007 | Berra et al. | 623/1.12 |
| 2008/0125715 A1 * | 5/2008 | Cohen | 604/164.13 |

FOREIGN PATENT DOCUMENTS

| | | | |
|---|---|---|---|
| EP | 1986573 | 11/2008 | |
| IE | 912606 | 1/1992 | |
| JP | 4236965 | 8/1992 | |
| JP | 2009/525139 | 7/2009 | |
| KR | 2009/0003163 | 1/2009 | |
| WO | WO 01/17602 A1 | 3/2001 | A61M 29/00 |
| WO | WO 0117602 | 3/2001 | |
| WO | WO 2007/092276 | 8/2007 | |
| WO | PCT/US2009/004126 | 7/2009 | |

* cited by examiner

INTRODUCER FOR ENDOVASCULAR IMPLANTS

RELATED APPLICATIONS

This application is a continuation of PCT/US2009/004126, filed Jul. 16, 2009, which claims priority to U.S. Provisional Application No. 61/135,263, filed on Jul. 18, 2008, each of which are incorporated by reference herein in their entirety.

TECHNICAL FIELD

The present invention relates to an introducer for the deployment of implants and prostheses into a body lumen of a patient and in particular for deploying a stent-graft or stent into a patient. The device is particularly suited for deployment of stent-grafts and stents in the aortic arch.

BACKGROUND

Prostheses for the repair of vascular defects, including for example vascular aneurysms, are well known in the art. A common prosthesis for treatment of such a medical condition is a stent-graft.

Prostheses of this type are typically deployed endoluminally through a vein or artery adjacent a surface of a patient. For example, aortic prostheses are commonly fed through the femoral artery. A common method of deployment involves the location of a guide wire along the path to be followed by the introducer assembly, up to the site in the vasculature to be treated. Once the guide wire is in place, a series of catheters is advanced along the guide wire, finally with the introduction of an inner catheter assembly which carries the stent or stent-graft to be fitted. The catheters have sufficient trackability to follow the guide wire along the curves and turns of the patient's vasculature and some can also curve sufficiently so as to be able to fit a stent-graft, for example, into the aortic arch of a patient.

In order to guide the inner catheter assembly through the tortuous path of the patient's vasculature and along the guide wire, the assembly is typically provided with a flexible tip, most commonly in the form of a dilator tip although in some cases in the form of a flexible distal end of the inner catheter itself. The dilator or catheter tip is formed of a flexible material able to curve so as to follow the path of the guide wire over which is slides.

The implant is usually restrained on the inner catheter by one or more restraining mechanisms. Once the introducer has been located in the correct position in the patient's vasculature, with the implant positioned at the treatment site, the deployment procedure is commenced, typically first by the retraction of an outer sheath of the assembly to bare the implant. In the case of a self-expanding implant, the next step involves releasing the restraining system, which causes immediate or progressive expansion and thus deployment of the implant, in dependence upon its design and the nature of the restraining mechanism. In the case of an implant which is separately expandable, such as by balloon, the expansion mechanism is actuated after removal of the outer sheath to affect this expansion.

As a result of tension in various parts of the introducer assembly, particularly in the case of self-expanding implants and also in the case of deployment in a curved lumen such as in the aortic arch, as the implant is being released this tension in the assembly is typically released also. This can often result in a jerking action of one or more of the components of the system. Where the implant is to be located in a curved part of a patient's vasculature, this can result in the inner catheter being urged forwardly during the implant release phase. This can cause the distal end of the introducer to prod into the wall of the vessel, causing tissue damage or trauma. This can result in complications to the medical procedure, both during the course of the procedure itself and subsequently to that during the body's attempt to heal the vessel, in some cases resulting in the generation of stenosis. Even though the dilator tip is flexible, when this is prodded straight into a wall of a patient's vasculature, it is relatively hard and sufficiently so to cause damage to the vessel wall. The skilled person will realize that the reason for this increased hardness of the dilator tip in such circumstances is that such motion, instead of pushing the tip to effect sideways bending thereof, seeks to compress the tip longitudinally.

BRIEF SUMMARY

In one embodiment, the present invention includes an endovascular introducer assembly having a dilator tip formed of a flexible material that has a distal end, a proximal end, and a natural unbiased condition where a lumen is formed within and extending the length of the dilator tip between the distal and proximal ends and a guide wire that is disposed in the lumen where the dilator tip includes a distal region adjacent to the distal end, a proximal region adjacent to the proximal end and an intermediate region that disposed between the distal and proximal regions, where the dilator tip has a first biased condition having a first biased radius of curvature when the dilator dip is disposed about the distal region of the guide wire, a second biased condition having a second biased radius of curvature when the dilator tip is disposed about the proximal region of the guide wire, and a third biased condition having a third biased radius of curvature when the dilator tip is disposed about the intermediate region of the guide wire, wherein the first biased radius of curvature is less than the third biased radius of curvature, the second biased radius of curvature is between the first and second biased radii of curvatures.

In another embodiment, the endovascular introducer assembly includes a dilator tip formed of a flexible material having a distal end and a proximal end and having a natural unbiased condition with a curvature of at least 180°, a lumen formed within and extending the length of the dilator tip between the distal and proximal ends, and a guide wire disposed through the lumen, where the guide wire has a distal region having a length of at least 4 cm and adjacent to a distal end, a proximal region adjacent to the proximal end and having a flexibility less than the distal region, and an intermediate region disposed between the distal and proximal regions and having a flexibility between the distal region and the proximal region, wherein the dilator tip has a first biased condition having a first biased radius of curvature when the dilator tip is disposed about the distal region of the guide wire where the dilator tip is curved by at least 90°, a second biased condition having a second biased radius of curvature when the dilator tip is disposed about the proximal region of the guide wire where the dilator dip is not curved by no more than 90°, and a third biased condition having a third biased radius of curvature when the dilator tip is disposed about the intermediate region of the guide wire, where the first biased radius of curvature is less than the third biased radius of curvature, the second biased radius of curvature is between the first and second biased radii of curvatures.

One method of deploying an endoluminal device in a patient includes providing an introducer assembly for introducing the endoluminal device into the patient, the assembly including a catheter having a dilator tip with a flexible distal end formed in a curve when in an unbiased condition, and a guide wire having a distal region, a proximal region having a flexibility less than the distal region, and an intermediate region disposed between the distal and proximal regions and having a flexibility between the distal region and the proximal region, where the distal region is more flexible than the dilator tip, where the method includes inserting the guide wire into the vasculature of a patient, placing the guide wire at the treatment site, feeding the catheter over the guide wire, placing the catheter at the treatment site, withdrawing the guide wire, aligning the distal region of the guide wire with the dilator tip to curve the dilator tip into a substantially U-shape, and releasing the endoluminal device from the introducer assembly.

BRIEF DESCRIPTION OF THE DRAWINGS

Embodiments of the present invention are described below, by way of example only, with reference to the accompanying drawings, in which.

DETAILED DESCRIPTION OF THE DRAWINGS AND THE PRESENTLY PREFERRED EMBODIMENTS

For the purposes of this disclosure, when used in connection with description of a stent-graft or other implantable device, the term "proximal" refers to a part or position closest to the heart, that is upstream in the direction of blood flow, while the term "distal" refers to a part or position furthest from the heart. On the other hand, when used in connection with an introducer assembly the term "proximal" refers to a position or part closest to the surgeon and typically kept outside the patient, while the term "distal" refers to a position or part furthest from the surgeon and in practice furthest into a patient during a deployment procedure.

The described embodiments also make reference to the deployment of a stent-graft in the aortic arch. The introducer could be used to deploy a wide variety of devices including, for example, stents, and can be used to deploy these devices in other parts of a patient.

Figure 1:
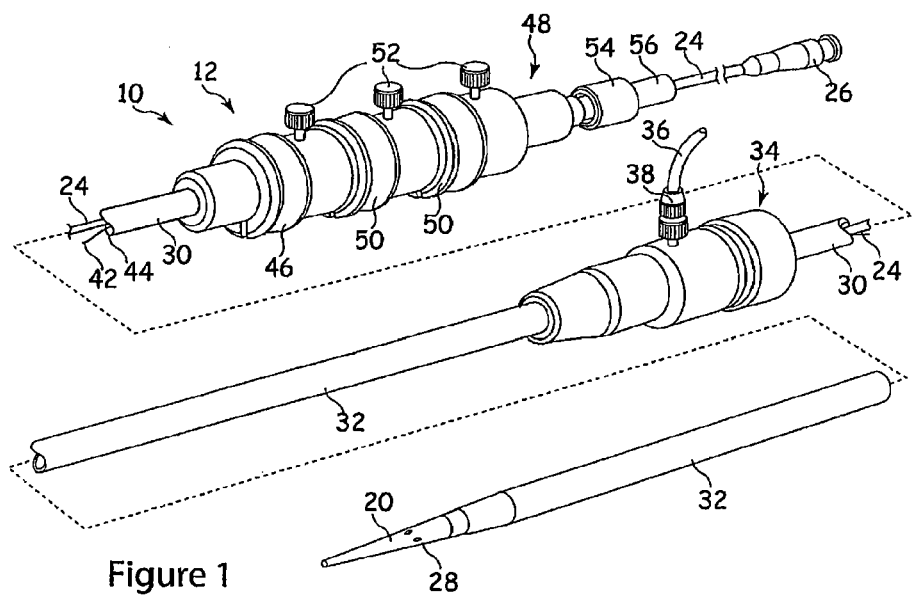
FIG. 1 is a perspective view of an example of introducer system which can be used with the present invention.
Figure 2:
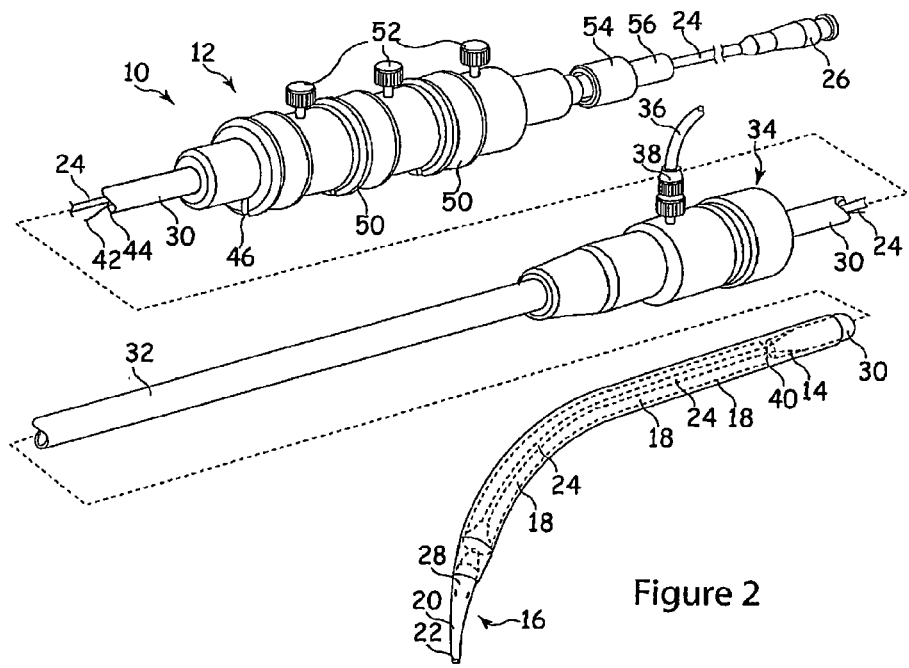
FIG. 2 is perspective view of another example of introducer system which can be used with the present invention.

Referring to FIGS. 1 and 2, the introducer 10 includes an external manipulation section 12, a distal attachment region 14 and a proximal attachment region 16. The distal attachment region 14 and the proximal attachment region 16 secure the distal and proximal ends of the implant 18, respectively. During the medical procedure to deploy the implant 18, the distal and proximal attachment regions 14 and 16 will travel through the patient's lumen to a desired deployment site. The external manipulation section 12, which is acted upon by a surgeon to manipulate the introducer, remains outside of the patient throughout the procedure.

The proximal attachment region 16 of the introducer 10 includes a dilator tip 20, which is typically provided with a bore 22 therein for receiving a guide wire (not shown) of conventional type. The longitudinal bore 22 also provides a channel for the introduction of medical reagents. For example, it may be desirable to supply a contrast agent to allow angiography to be performed during placement and deployment phases of the medical procedure.

A guide wire catheter 24, conventionally made from a flexible thin walled metal tube, is fastened to the dilator tip 20. The guide wire catheter 24 is flexible so that the introducer 10 can be advanced along a relatively tortuous vessel, such as a femoral artery, and so that the distal attachment region 14 can be longitudinally and rotationally manipulated. The guide wire catheter 24 extends through the introducer 10 to the external manipulation section 12, terminating at a connection device 26, in conventional manner.

The connection device 26 is designed to accept a syringe to facilitate the introduction of reagents into the inner guide wire catheter 24. The guide wire catheter 24 is in fluid communication with apertures 28 in the flexible dilator tip 20. Therefore, reagents introduced into connection device 26 will flow to and emanate from the apertures 28.

A pusher sheath or rod 30 (hereinafter referred to as a pusher member), typically made from a plastics material, is mounted coaxial with and radially outside of the guide wire catheter 24. The pusher member 30 is "thick walled", that is the thickness of its wall is preferably several times greater than that of the guide wire catheter 24.

A sheath 32 extends coaxially over and radially outside of the pusher member 30. The pusher member 30 and the sheath 32 extend distally to the external manipulation section 12.

The implant 18, which may be a stent, a stent-graft or any other implant or prosthesis deliverable by this introducer 10, is retained in a compressed condition by the sheath 32. The sheath 32 extends distally to a sheath manipulator and haemostatic sealing unit 34 of the external manipulation section 12. The haemostatic sealing unit 34 includes a haemostatic seal (not shown) and a side tube 36 held to the sealing unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher member 30. The luer lock 38 facilitates the introduction of medical fluids between the pusher member 30 and the sheath 32. Saline solution is typically used.

During assembly of the introducer 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher member 30 and retains a distal end 40 of the implant 18 during the procedure. The distal end of the implant 18 is provided with a loop (not shown) through which a distal trigger wire 42 extends. The distal trigger wire 42 also extends through an aperture (not shown in FIGS. 1 and 2) in the pusher member 30 into an annular region 44 between the inner guide wire catheter 24 and the pusher member 30. The distal trigger wire 42 extends through the annular region 44 to the external manipulation section 12 and exits the annular region 44 at a distal wire release mechanism 46.

A proximal portion of the external manipulation section 12 includes at least one release wire release mechanism 50 mounted on a body 48, in turn mounted onto the pusher member 30. The guide wire catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal release wire release mechanism 50 must be moved before the distal wire release mechanism or mechanisms 46 can be moved. Therefore, the distal end of the implant 18 cannot be released until a self-expanding zigzag stent thereof has been released. Clamping screws 52 prevent inadvertent early release of the implant 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the guide wire catheter 24. When the vise jaws are engaged, the guide wire catheter 24 can only move with the body 48 and hence it can only move with the pusher member 30. With the screw cap 56 tightened, the entire assembly can be moved together as one piece.

Once the introducer assembly 10 is in the desired deployment position, the sheath 32 is withdrawn to just proximal of the distal attachment region 14. This action releases the middle portion of the implant 18, in this example a stent or stent-graft, so that it can expand radially. Consequently, the implant 18 can still be rotated or lengthened or shortened for accurate positioning. The proximal end of the implant 18 however, is still retained at the proximal attachment region 16 by means of the release wires. Also, the distal end of the implant 18 will still retained within the sheath 32.

Next, the pin vise 54 is released to allow small movements of the guide wire catheter 24 with respect to the pusher member 30 to allow the implant 18 to be lengthened, shortened, rotated or compressed for accurate placement in the desired location within the lumen. X-ray opaque markers (not shown) may be placed along the implant 18 to assist with placement of the prosthesis.

When the proximal end of the implant 18 is in place, the proximal trigger wire is withdrawn by distal movement of the proximal release wire release mechanism 50. The proximal wire release mechanism 50 and the proximal trigger wire 42 (I have 42 as distal trigger wire) can be completely removed by passing the proximal wire release mechanism 50 over the pin vise 54, the screw cap 56 and the connection device 26.

Next, the screw cap 56 of the pin vise 54 is loosened, after which the inner guide wire catheter 24 can be pushed in a proximal direction to move the dilator tip 20 in a proximal direction. When the dilator tip 20 no longer surrounds the end of the implant 18, it expands to engage the lumen walls of the patient. From this stage on, the proximal end of the implant 18 cannot be moved again.

Once the proximal end of the implant 18 is anchored, the sheath 32 is withdrawn distally of the distal attachment region 14, which withdrawal allows the distal end of the implant 18 to expand. At this point, the distal end of the implant 18 may still be repositioned as needed.

Figure 3:
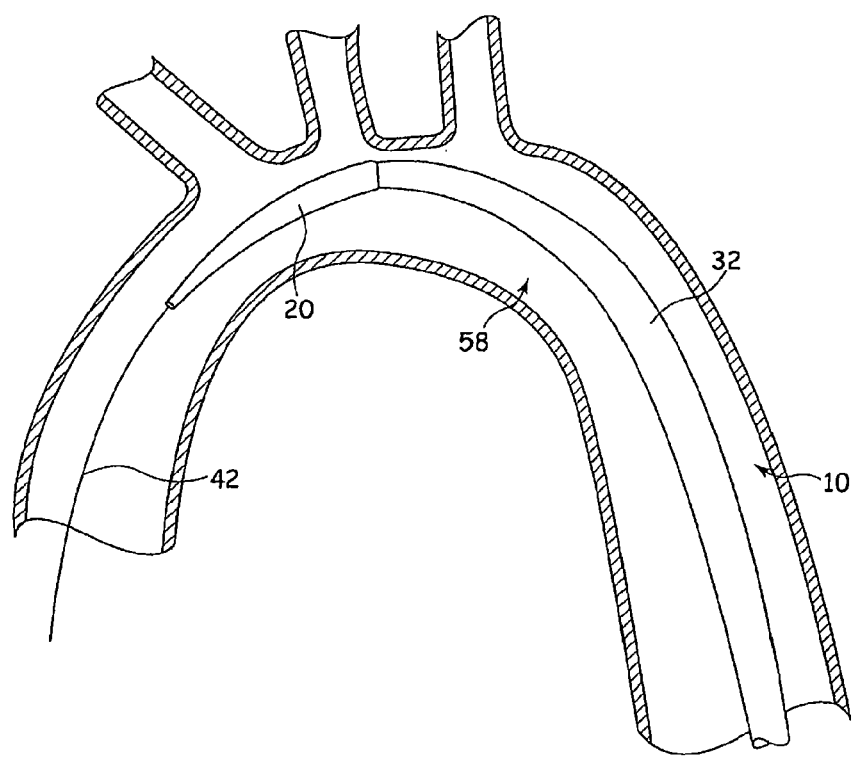
FIG. 3 is a prior art introducer system used to deploy an intraluminal device.

Referring next to FIG. 3, there is shown in schematic form the deployment of the introducer of FIGS. 1 and 2 into the aortic arch of a patient. The distal trigger wire 42, having been inserted first, tracks the introducer assembly around the curve of the aortic arch, including to some extent the substantially straight dilator tip 20.

Figure 4:
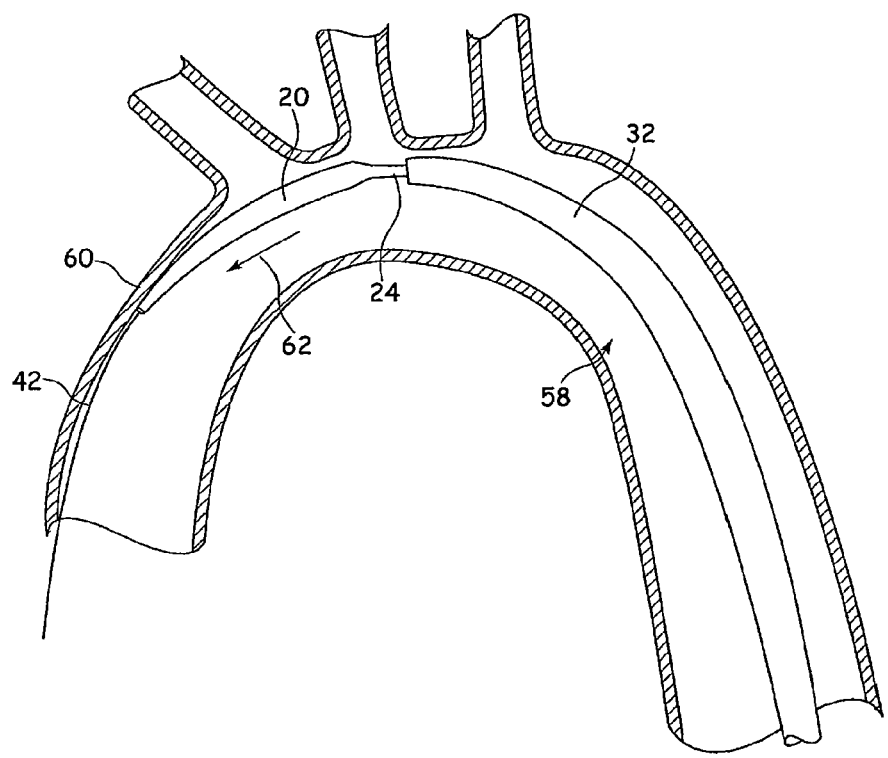
FIG. 4 is the prior art introducer system of FIG. 3 in the process of deploying the intraluminal device.

FIG. 4 shows the assembly of FIG. 3 just after initiation of the release phase. There are a number of occasions during the deployment phase where tension within the assembly is suddenly released. The first of these occurs during initial retraction of the outer sheath 32 from the dilator tip 20, whereupon the dilator tip 20 becomes free from the retraining force, typically a straightening force, of the outer sheath 32 as well as the fact that it is necessary to overcome an initially high friction between the outer sheath 32 and the internal components of the assembly 10 at the start of the deployment procedure, which can result in the whole assembly being pushed forwardly by the operating personnel. Other instances occur during release of the implant 18 from the introducer and in particular when the last restraining mechanism is released allowing the implant to separate from the introducer. This also releases the inner guide wire catheter 24 from its restraint on the implant 18.

As a result of these effects, the dilator tip 20 can jolt forwardly, as shown in FIG. 4, with the possibility that it can prod against the wall 60 of the patient's lumen 58. This can cause trauma and damage to the vessel wall leading in some instances to medical complications, including stenosis.

As can be seen in FIG. 4 in particular, it can be seen that the dilator tip 20 is substantially straight. When this moves forwards, in the direction of the arrow 62, it is much harder as the impact is in a compressive direction rather than in a radial bending direction. It is this characteristic which can cause the dilator tip 20 to damage the vessel wall.

The embodiments described below seek to provide a solution to this problem.

Figure 5:
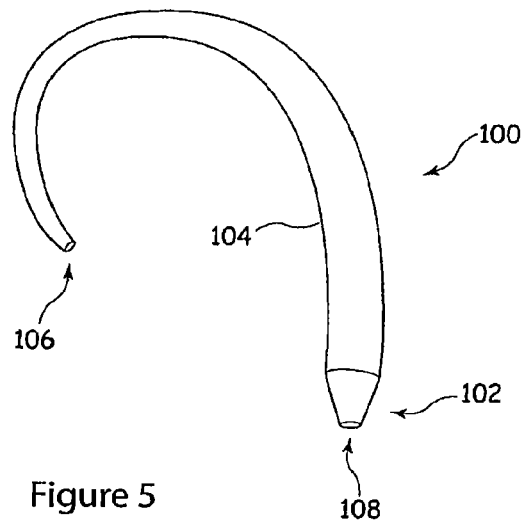
FIG. 5 is one embodiment of the present invention in its natural state.

Referring first to FIG. 5, there is shown an embodiment of dilator tip 100. The tip has a proximal end 102 which is securable to an inner guide wire catheter 24 and which is typically provided with one or more restraining wire tying locations. The body 104 of the dilator tip 100 tapers gently from its proximal end 102 to the distal point 106 so as to make the tip progressively more flexible along its length towards its tip for trackability purposes. The dilator tip 100 is provided with a lumen 108 therein, which extends throughout its length, for receiving a guide wire.

This dilator tip 100 differs from the dilator tip 20 of the example of FIGS. 1 and 2 in that is it formed to have a natural curvature, that it when in an unbiased condition. This curvature may be at least 90° but in the preferred embodiment is at least 180°, that is to give the dilator tip 100 a U-shape, and most preferably in the form of a pig tail, that is 360° or more. Curving the dilator tip to such an extent results in the tip in effect pointing backwardly during an implant release phase and thus providing no risk whatsoever of the point 106 jutting forwardly into a vessel wall.

In the embodiment of FIG. 5, the curvature of the dilator tip 100 is greater than 180° so that the point 106 is directed inwardly of the dilator tip 100, that is to point towards the proximal end 102. This has the advantage of hiding the tip from the vessel walls during the deployment operation. In practice, the curvature of the dilator tip 100 can be anything up to around 360° or more.

The dilator tip 100 can be manufactured for conventional materials, such as polyurethane. Its curvature can be formed during the extrusion, molding or casting processes, in manners which will be evident to the person skilled in the art and which therefore need not be described in detail herein.

Figure 6:
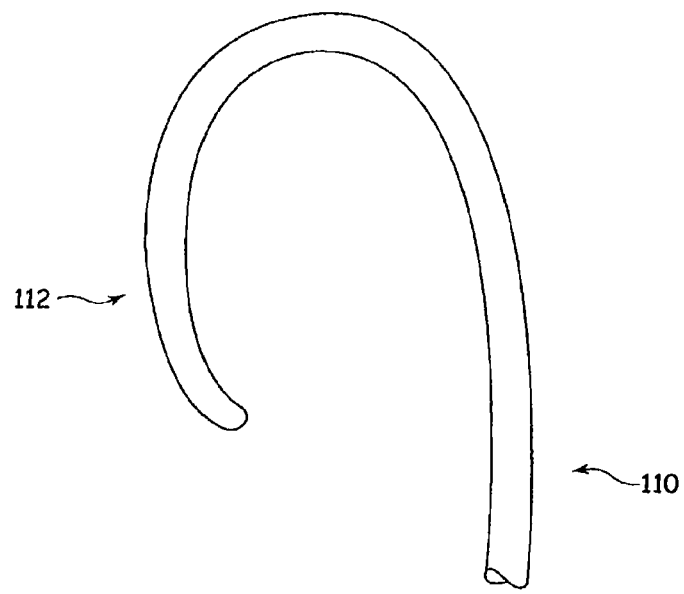
FIG. 6 is another embodiment of the present invention in its natural state.

FIG. 6 shows another example of curved introducer end, in this case being the distal end 112 of an inner catheter 110. This can be used, for example, in introducers provided with no dilator tip 20 of the type shown in FIGS. 1 and 2. In this instance, the proximal end 102 of the inner catheter, on which the implant is carried, is given a curvature similar to that of the dilator tip 100 of FIG. 5 so as to provide it with analogous characteristics.

The guide wire 142 for use with a dilator tip 100 or inner catheter 110 of the types shown in FIGS. 5 and 6 can be of conventional form, typically provided with a soft distal end and a stiffer body portion, the latter for trackability and the former for training the introducer during its insertion into the vasculature of the patient. However, in the preferred embodiments, the very flexible distal end 120 of the guide wire 142 is longer than in conventional guide wires, for example, 4 cm or more. This ensures that the distal end 120 of the guide wire 142 is long enough for the dilator tip 100 and in particular to ensure that the latter can curve throughout its length without being constrained to a straighter configuration by any of the stiffer part of the guide wire. Typically, the guide wire is formed of a relative stiff core rod which is covered at least at its distal end with a coil wrapped there around. The rod tapers towards the distal end, thereby becoming more flexible towards that direction, and the coiled element extends beyond the rod. The coil itself provides very little lateral restraining force, in other words is very soft and compliant.

FIGS. 7 to 14 show a series of stages of the deployment procedure of an introducer during a prototype trial.

Figure 7:
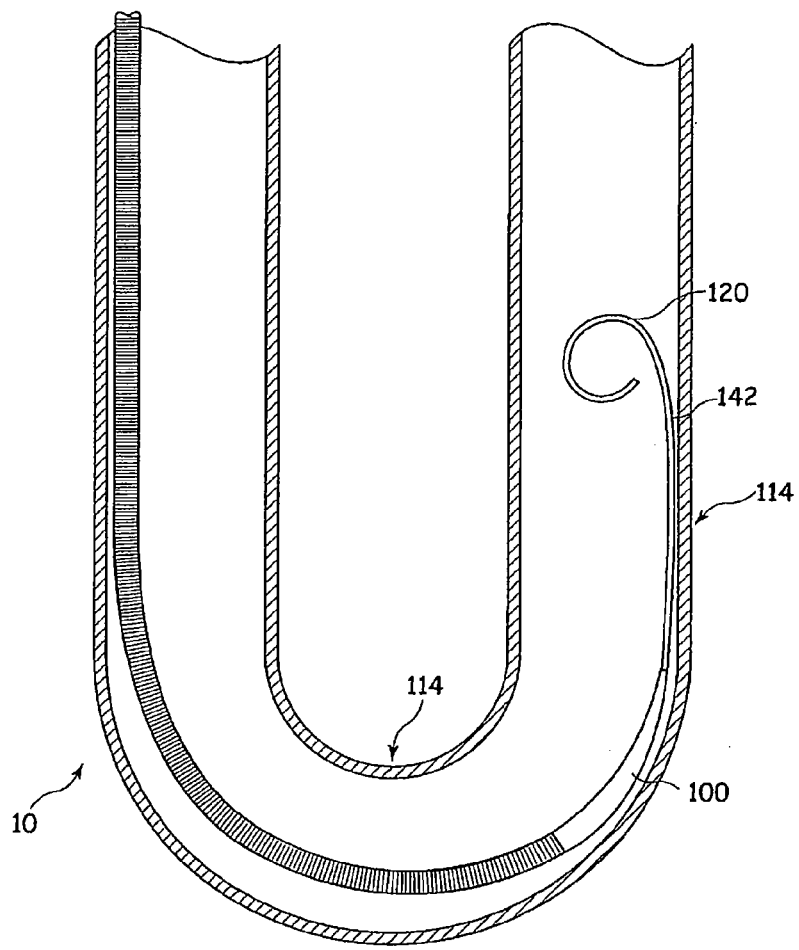
FIG. 7 is a perspective view of an introducer system including a dilator tip of the present invention shown in FIG. 5 positioned within the vasculature of a patient to deploy stent-graft.

In FIG. 7, the introducer assembly 10, provided with a dilator tip 100 of the type shown in FIG. 5, has been inserted into a curved vessel 114, in this case representative of the aortic arch of a human. The guide wire 142, which has a very flexible distal end 120, is introduced first and then the introducer assembly 10 fed over this to the treatment site. In this particular example, the treatment site is at the point of point of maximum curvature of the vessel 114.

The dilator tip 100 of the introducer 10 is substantially straight, as a result of being trained to this configuration by the relative stiffness of the guide wire 142, and in particular follows the path of the guide wire 142.

Figure 8:
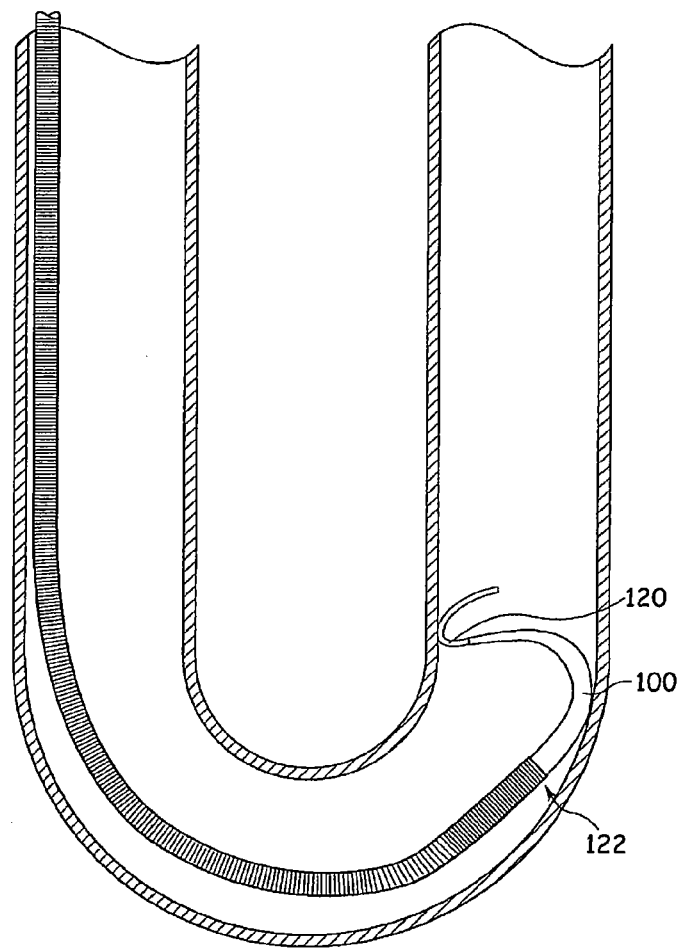
FIG. 8 depicts the introducer system shown in FIG. 7 where the dilator tip has a semi-curved shape.
Figure 9:
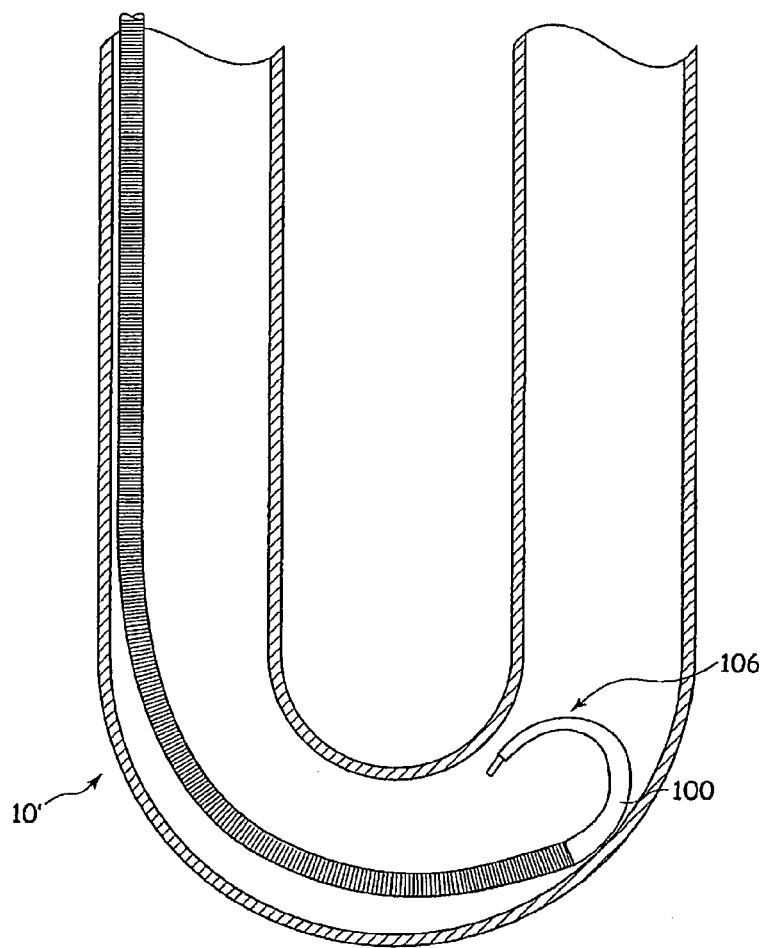
FIG. 9 depicts the introducer system shown in FIG. 7 where the dilator tip has a curved shape.

Referring next to FIG. 8, once the distal end 122 of the introducer 10 has been located at the desired position, before the deployment phase is commenced, the guide wire 142 is retracted until its very flexible distal end 120 slides into the dilator tip 100. As can be seen in particular in FIGS. 8 and 9, when this occurs and when the dilator tip 100 is no longer being biased to a straighter configuration by the stiffer body portion of the guide wire 142, it can flex back to its natural curved condition. When this occurs, the point 106 of the dilator tip 100 is moved so as to point backwardly and, importantly, out of the way of any part of the vessel wall forward of the distal end of the introducer 10.

Figure 10:
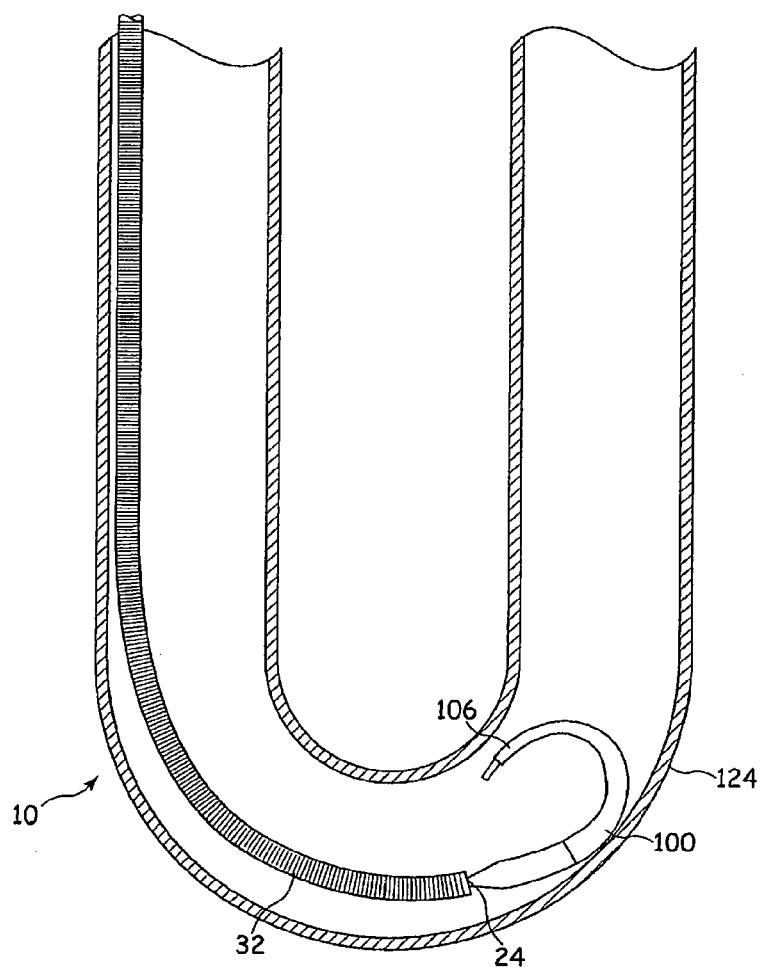
FIG. 10 depicts the introducer system shown in FIG. 7 where the sheath is being retracted to deploy the stent-graft.

Referring to FIG. 10, in this view, the outer sheath 32 has been pulled back a little, at the start of the phase which withdraws this to bare the enclosed implant. At this stage, the guide wire catheter 24 is released from the straightening force of the outer sheath 32, which can cause the dilator tip 100 to jump forwardly. As can be seen in FIG. 10, in fact, the distal tip may come into contact with the vessel wall 124 but only at a curved side of the dilator tip 100. The point 106 is well hidden by virtue of the curvature of the dilator tip 100. In the preferred embodiment the dilator tip 100 curves by 360° or more, which allows the guide wire 142 still to extend along the lumen yet to protect the lumen walls from the point 106.

Figure 11:
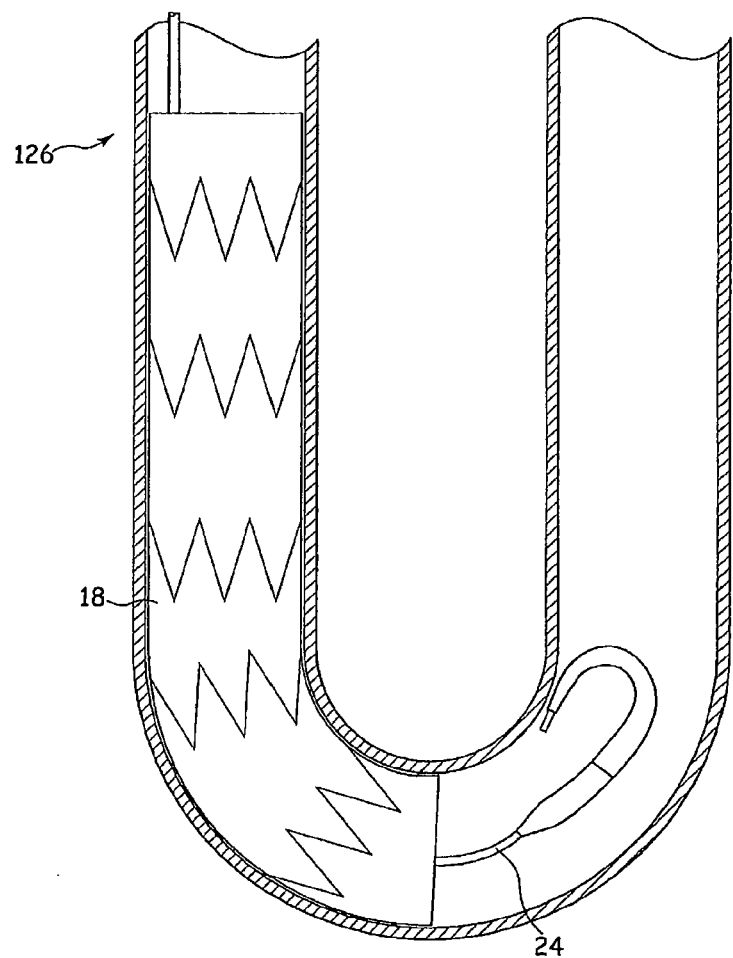
FIG. 11 depicts the introducer system shown in FIG. 7 where the stent-graft is partially deployed.

In FIG. 11 the outer sheath 32 has been completely withdrawn from the implant, in this case a stent-graft, and the latter has been almost completely released from the inner guide wire catheter 24, being retained only at its distal end 126 by means of one or more restraining wires (not shown) of conventional form.

Figure 12:
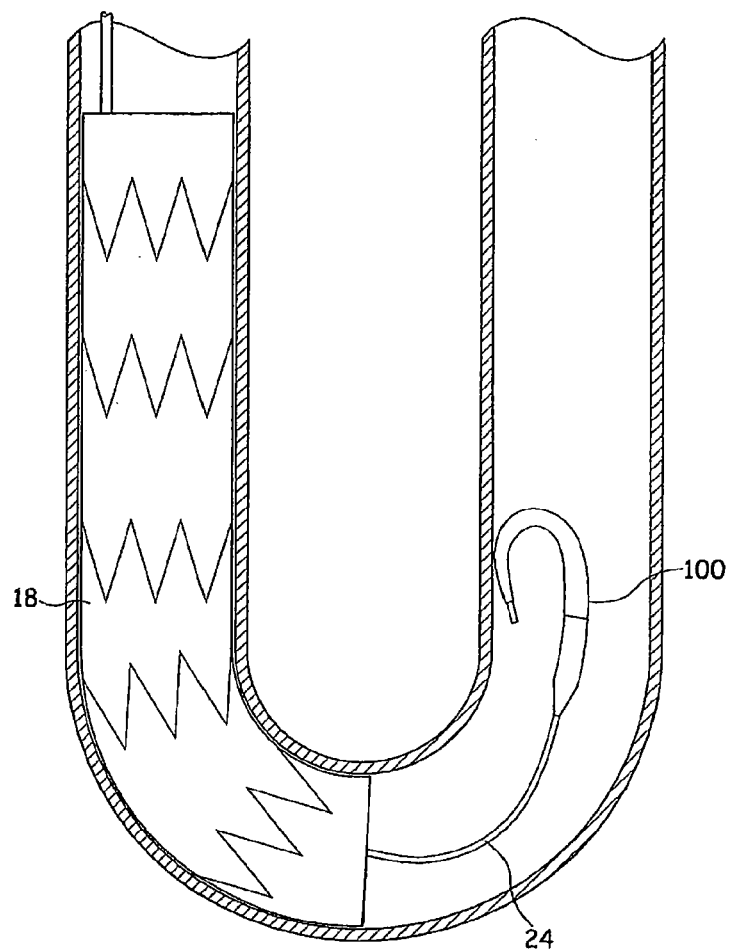
FIG. 12 depicts the introducer system shown in FIG. 7 where the stent-graft is fully deployed.

The final release of the implant 18 from the introducer causes another possible instance of jumping of the inner catheter assembly as this becomes released from its constraint to the implant. As can be seen in FIG. 12, the inner guide wire catheter 24 and dilator tip 100 have shot forward along the vessel. Again, however, due to the curve in the dilator tip 100, if this comes into contact with the vessel wall 124 it is only at a curved part, which does not cause damage or trauma to the vessel wall and which assists in the dilator tip 100 sliding along the vessel wall 124 to release the tension in the inner guide wire catheter 24.

Figure 13:
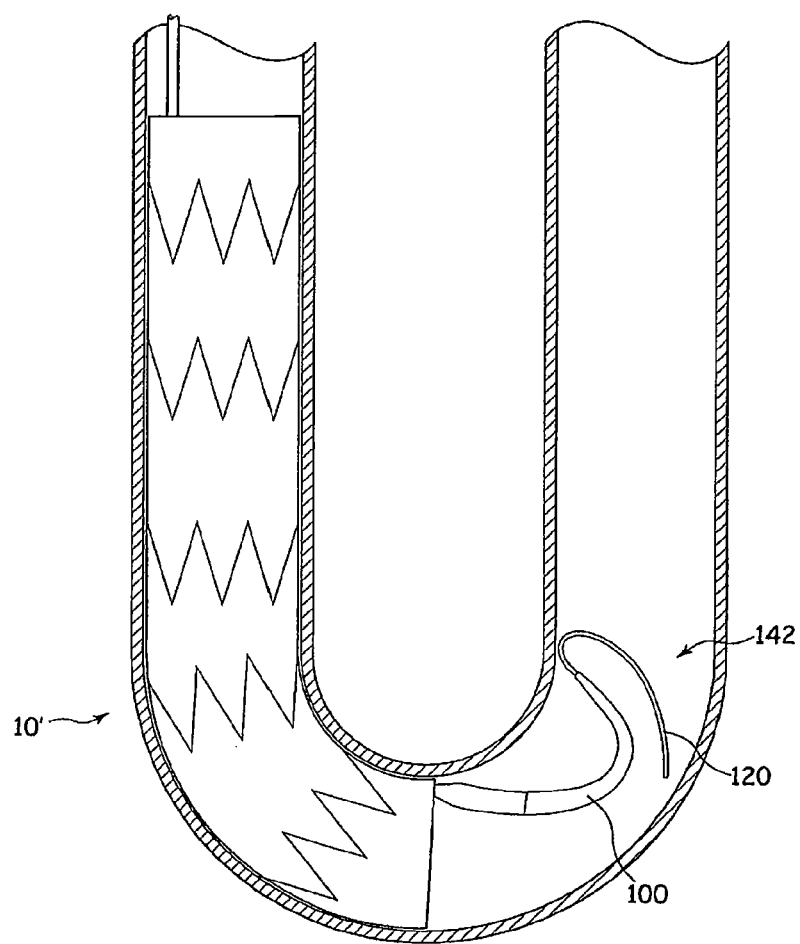
FIG. 13 depicts the introducer system shown in FIG. 7 where the dilator tip is being retracted along a guide wire in the process of being removed from the patient's vasculature.
Figure 14:
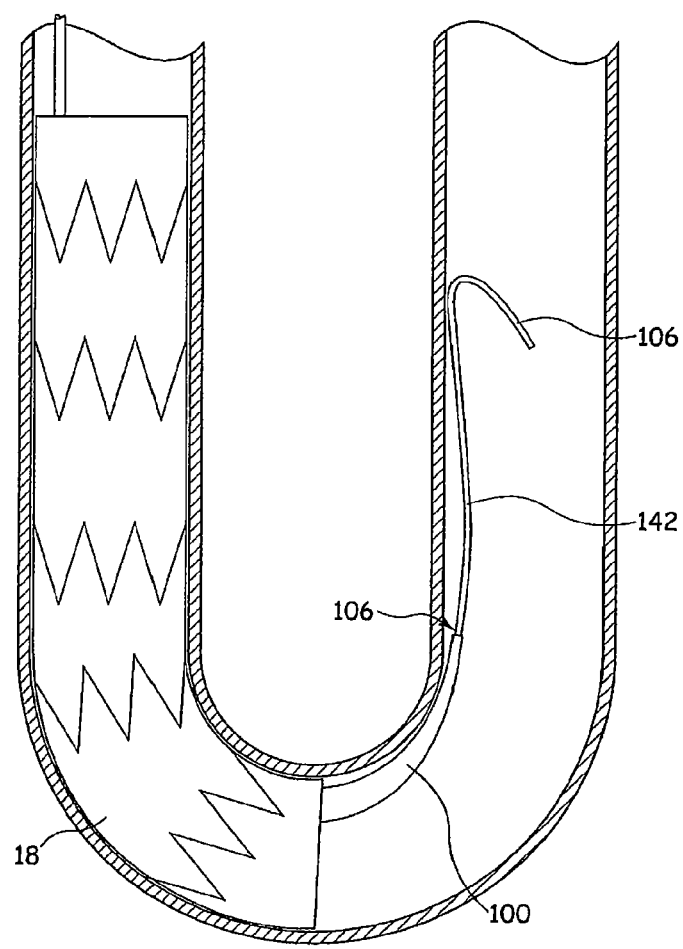
FIG. 14 depicts the introducer system shown in FIG. 7 where the dilator tip is being further retracted along the guide wire in the process of being removed from the patient's vasculature.

FIGS. 13 and 14 show the final stage of the deployment process. The guide wire 142 is moved forward again to push its soft distal end 120 out of the distal end of the introducer 10 and thus to push into the dilator tip 100 a more rigid part of the guide wire 142. This causes the dilator tip 100 to straighten again, as can be seen in FIG. 14 in particular, whereupon the inner catheter 110 can be removed from the patient's lumen without any risk of the point 106 of the dilator tip 100 snagging on the implant.

FIGS. 7 to 14 show an example of use of an introducer having a curved dilator tip 100. Operation of an introducer having a curved distal end to the inner catheter 110 thereof will be analogous to FIGS. 7 to 14 and readily appreciated by the skilled person.

Figure 15:
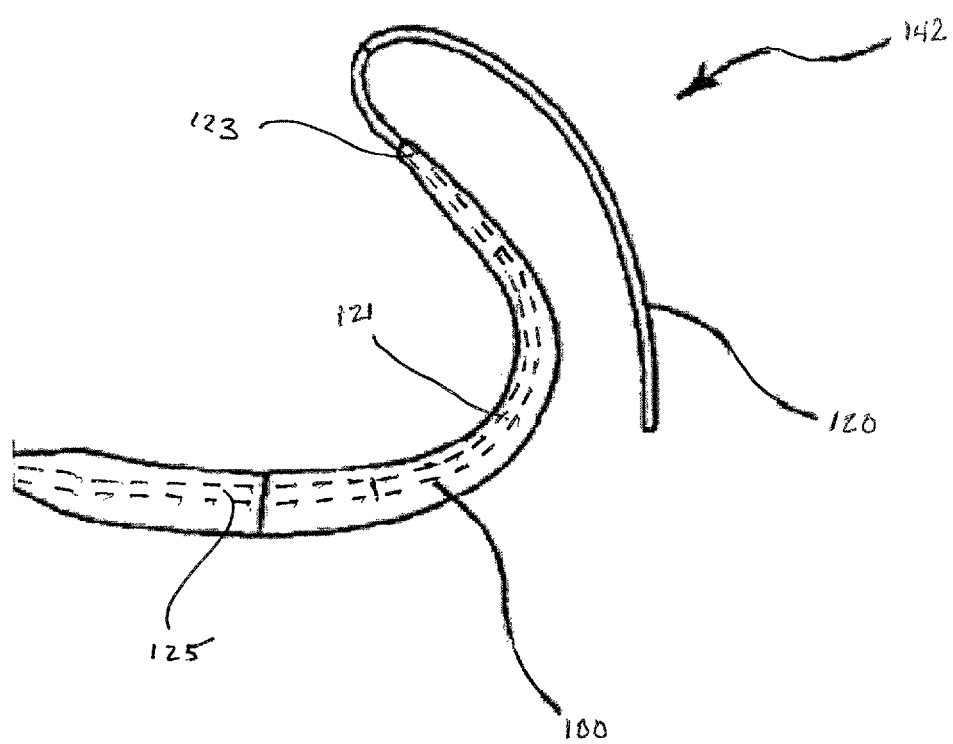
FIG. 15 depicts an introducer system with a guide wire having various regions of variable stiffness.

The above-described embodiments make use of a guide wire 142 which has a soft distal end 120 to allow the dilator tip 100 or the distal end of the inner catheter 110 to curve. In some embodiments, as shown in FIG. 15, the guide wire 142 may be formed with a soft portion 121 part way along its length, which portion is intended to be aligned with the dilator tip 100 or distal end of the inner catheter 110 so as to allow these to curve while still retaining a length of guide wire 142 extending beyond the distal end of the introducer assembly. Thus, the soft portion 121 would be bounded either end by stiffer portions 123, 125 of guide wire 142. The distal end or dilator tip 100 can be allowed to curve or straighten by moving the guide wire 142 into or out of the dilator tip/distal end so as to bring the soft and stiffer parts of the guide wire 142 into the dilator tip/distal end as required.

It will be appreciated also that it is not necessary to have a particular structure of guide wire 142 as the straightening effect of the wire guide would be removed simply by withdrawing the guide wire 142 beyond the dilator tip 100 or distal end of the guide wire catheter 24.

The invention claimed is:

1. An endovascular introducer assembly, the introducer assembly comprising:
   a guide wire catheter having a distal end, a dilator tip disposed at the distal end of the guide wire catheter and formed of a flexible material, the dilator tip having a distal end, a proximal end, a region between the distal end and the proximal end, and a natural curved condition between the distal end and the proximal end of the dilator tip;
   a guide wire lumen formed within and extending through the dilator tip between the distal and proximal ends of the dilator tip; and
   a guide wire disposable within the guide wire lumen comprising,
      a distal region adjacent to the distal end,
      a stiffer proximal region, and
      an intermediate region adjacent to the distal region and the stiffer proximal region, where the intermediate region is more flexible than the distal region and stiffer proximal region,
   wherein the dilator tip comprises,
   a first condition where the stiffer proximal region of the guide wire is disposed in the guide wire lumen from the proximal end to the distal end of the dilator tip; and
   a second condition where the intermediate region of the guide wire is disposed through the guide wire lumen from the proximal end to the distal end of the dilator tip, and the dilator tip is in a curved condition wherein the dilator tip is curved at least 90°.

2. The endovascular introducer assembly of claim 1 wherein the distal region of the guide wire is more flexible than the stiffer proximal region the guide wire.

3. The endovascular introducer assembly of claim 1 wherein the dilator tip is substantially straight when in the first condition.

4. The endovascular introducer assembly of claim 1, wherein the dilator tip has a length of between 2 and 14 cm.

5. The endovascular introducer assembly of claim 1 wherein the distal region of the guide wire is at least 4 cm in length.

6. An endovascular introducer assembly, the introducer assembly comprising:
   a guide wire catheter having a distal end, a dilator tip disposed at the distal end of the guide wire catheter and formed of a flexible material, the dilator tip having a distal end, proximal end, a region between the distal end and the proximal end, and a natural curved condition between the distal end and the proximal end of the dilator tip;
   a guide wire lumen formed within and extending through the dilator tip between the distal and proximal ends of the dilator tip; and
   a guide wire disposable within the guide wire lumen comprising,
      a distal region having a length of at least 4 cm,
      a stiffer proximal region, and
      an intermediate region adjacent to the distal region and the stiffer proximal region, where the intermediate region is more flexible than the distal region and stiffer proximal region
   wherein the dilator tip comprises,
   a first condition where the stiffer proximal region of the guide wire is disposed in the guide wire lumen from the proximal end to the distal end of the dilator tip where the dilator tip is curved;
   a second condition where the intermediate region of the guide wire is disposed through the guide wire lumen from the proximal end to the distal end of the dilator tip, and the dilator tip is in its natural curved condition wherein the dilator tip is curved at least 180°.

7. The endovascular introducer assembly of claim 6 wherein the dilator tip is curved by no greater than 180° when in the first condition.

8. The endovascular introducer assembly of claim 6 wherein the dilator tip has a generally U-shape when in the second condition.

9. The endovascular introducer assembly of claim 6 wherein the intermediate region of the guide wire is more flexible than the dilator tip.

10. The endovascular introducer assembly of claim 6 where the stiffer proximal region of the guide wire is less flexible than the dilator tip.

11. The endovascular introducer assembly of claim 6 wherein the intermediate region of the guide wire is at least as long as the dilator tip.

12. The endovascular introducer assembly of claim 11 wherein when in the first condition the dilator tip is substantially linear.

13. An endovascular introducer assembly, the introducer assembly comprising:
   a guide wire catheter having a distal end, a dilator tip disposed at the distal end of the guide wire catheter and formed of a flexible material, the dilator tip having a distal end, a proximal end, a region between the distal end and the proximal end, and a natural curved condition between the distal end and the proximal end of the dilator tip;
   a guide wire lumen formed within and extending through the dilator tip between the distal and proximal ends of the dilator tip; and
   a guide wire disposable within the guide wire lumen comprising,
      a distal region,
      a stiffer proximal region, and
      an intermediate region adjacent to the distal region and the stiffer proximal region, where the intermediate region is more flexible than the distal region and stiffer proximal region,
   wherein the dilator tip comprises,
   a first condition where the stiffer proximal region of the guide wire is disposed in the guide wire lumen from the proximal end to the distal end of the dilator tip; and
   a second condition where the intermediate region of the guide wire is disposed in the guide wire lumen from the proximal end to the distal end of the dilator tip, wherein the dilator tip is curved at least 180°.

14. The endovascular introducer assembly of claim 13 wherein the dilator tip is curved by at least 270° when in the natural curved condition.

* * * * *